United States Patent [19]

Muller et al.

[11] 4,029,724
[45] June 14, 1977

[54] METHOD OF AND APPARATUS FOR MIXING GAS INTO LIQUIDS FOR CULTIVATING MICROORGANISMS

[75] Inventors: Hans Muller, Erlenbach, Zurich; Bruno Guazzone, Rapperswil, both of Switzerland

[73] Assignee: Hans Muller, Mannedorf, Switzerland

[22] Filed: June 25, 1976

[21] Appl. No.: 699,709

Related U.S. Application Data

[63] Continuation of Ser. No. 529,132, Dec. 3, 1974, abandoned.

[30] Foreign Application Priority Data

Dec. 4, 1973  Switzerland ............. 16819/73

[52] U.S. Cl. ............................. 261/87; 195/109; 195/142; 195/143; 261/93; 261/DIG. 75
[51] Int. Cl.² .................................. B01F 3/04
[58] Field of Search .......... 261/36 R, 77, 87, 88, 261/93, 123, DIG. 75; 195/109, 142–144; 209/169

[56] References Cited
UNITED STATES PATENTS

| | | | |
|---|---|---|---|
| 2,246,559 | 6/1941 | Weinig | 261/93 |
| 2,892,543 | 6/1959 | Daman | 261/93 X |
| 2,944,802 | 7/1960 | Daman | 261/87 |
| 3,017,951 | 1/1962 | Wiley | 261/93 X |
| 3,066,921 | 12/1962 | Thommel et al. | 261/87 X |
| 3,210,053 | 10/1965 | Boester | 261/93 X |
| 3,393,802 | 7/1968 | Logue et al. | 261/87 X |
| 3,584,840 | 6/1971 | Fuchs | 261/87 X |
| 3,625,834 | 12/1971 | Muller | 261/93 X |
| 3,650,950 | 3/1972 | White | 261/87 X |
| 3,865,910 | 2/1975 | Hori | 261/93 |

FOREIGN PATENTS OR APPLICATIONS

| | | | |
|---|---|---|---|
| 48,730 | 5/1934 | Denmark | 261/93 |
| 1,474,582 | 3/1967 | France | 261/87 |

Primary Examiner—Tim R. Miles
Assistant Examiner—Richard L. Chiesa
Attorney, Agent, or Firm—Michael J. Striker

[57] ABSTRACT

A vessel is provided for cultivating microorganisms. Said vessel contains a body of liquid, and a hollow rotary impeller is mounted in the vessel and has in the region of its axis of rotation a liquid inlet formed with a venturi-shaped constriction. A plurality of first gas outlets communicate with the liquid inlet in the region of the constriction so that the suction resulting from the liquid flow will pull the gas through these first outlets. A plurality of second gas outlets are located on the periphery of the impeller remote from the first outlet.

10 Claims, 4 Drawing Figures

METHOD OF AND APPARATUS FOR MIXING GAS INTO LIQUIDS FOR CULTIVATING MICROORGANISMS

CROSS REFERENCE TO RELATED APPLICATION

This is a continuation of application Ser. No. 529,132 now abandoned, filed Dec. 3, 1974.

BACKGROUND OF THE INVENTION

The present invention relates generally to the mixing of gas into liquids, and more particularly to a novel method of obtaining such mixing and to an arrangement for carrying out the method.

There are many instances where it is necessary to mix gas or gases into liquids. One of these is, the aeration of liquid nutrient media in the growing of microorganisms and, the harvesting of the metabolic products of such microorganisms. Said mixing also is needed e.g. for various chemical gas reactions. There are, in fact, a great number of applications where gas must be as finely dispersed as possible in a liquid. Devices for obtaining such gas dispersions in liquids are already known. For example, it is known to provide a vessel in its interior with a hollow impeller that is mounted for rotation and has located adjacent its axis an inlet formed with a venturi-like constriction. When the impeller rotates the liquid is drawn in through the constriction and is expelled at or near the periphery of the expeller back into the vessel. Outlet openings for gas are provided in the impeller in the region of the throat of the venturi-like constriction so that the suction which results in this region from the flow of liquid is communicated to these outlet openings which in turn communicate with a source of gas, whereby the gas is drawn into the liquid and becomes admixed therewith.

This arrangement has the advantage that the formation of a liquid-gas dispersion is possible without requiring the use of expensive compressors, and that in fact a suction effect is obtained in the throat of the venturi-like constriction. This means that the expenses involved with having to pressurize the gas is in the prior art, are avoided in this arrangement.

However, it has been found that while this device is very advantageous, it is not always suitable in various applications. The efficiency of the device, that is the amount of gas which it is able to introduce into the liquid, is sometimes not adequate for a particular requirement, especially if two or more different gases must be admitted into the liquid which have to be kept separated until they are actually injected into the liquid. Such a requirement exists, for example, when yeast is to be obtained from methane as the carbon source, so that the methane and in addition air must be admitted into liquid. It is known that within a wide range of mixtures a combination of methane and air forms an explosive mix so that a separate admission of methane and air into the liquid is absolutely essential for safety reasons. Evidently, this is not possible with the prior-art device described above. Another drawback of this device is that in many instances the amount of gas that can be admitted into the liquid via the gas outlets that discharge into the throat of the venturi-like constriction, is simply not adequate for a particular requirement.

SUMMARY OF THE INVENTION:

It is an object of the invention to overcome the disadvantages of the prior art.

More particularly, it is an object of the invention to provide an improved method of admitting increased quantities of gas or gases into a liquid to form a gas dispersion therein, but without requiring prior pressurizing of the gas or gases.

Another object of the invention is to provide an apparatus for carrying out the novel method.

In keeping with these objects, and with others which will become apparent hereafter, one feature of the invention resides in an apparatus for mixing gas into liquids, and more particularly in a combination in such an apparatus which comprises a vessel for a liquid, and a hollow rotary impeller in this vessel and having in the region of its axis of rotation a liquid inlet formed with a venturi-shaped construction, a plurality of first gas outlets adapted to communicate with a source of gas and located in the region of the liquid inlet, and a plurality of second gas outlets also adapted to communicate with a source of gas but being spaced on the impeller from the first gas outlets.

Each of the gas outlets of the first and second plurality belongs to a different gas supplying system. In the system having the first gas outlets the admission and admixture of the gas takes place in the manner known from the prior art, in that the suction which develops at the throat of the venturi-shaped constriction draws the gas through the first outlets so that it becomes admixed with the liquid flowing through the liquid inlet. As far as the second outlets of the other system are concerned, they discharge their gas into the liquid at a location remote from the first outlets, preferably on or in the region of the periphery of the impeller. It is advantageous if these second gas outlets diverge in a funnel-shaped configuration and face in the direction opposite to the direction of rotation of the impeller.

The cross-sections for the gas admission conduits communicating with the first and second outlets may be controlled, that is restricted or increased in usual manner by means of valves or the like, in order to control the gas flow therethrough. A very simple manner of doing this is to install throttles in these supply conduits which makes it possible to effect a control of the gas flow even while the arrangement is in operation, so that it is not necessary to provide complicated adjusting mechanisms within the arrangement itself, but rather the throttles can be located exteriorly of the arrangement, that is outside the vessel.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

Figure 1:
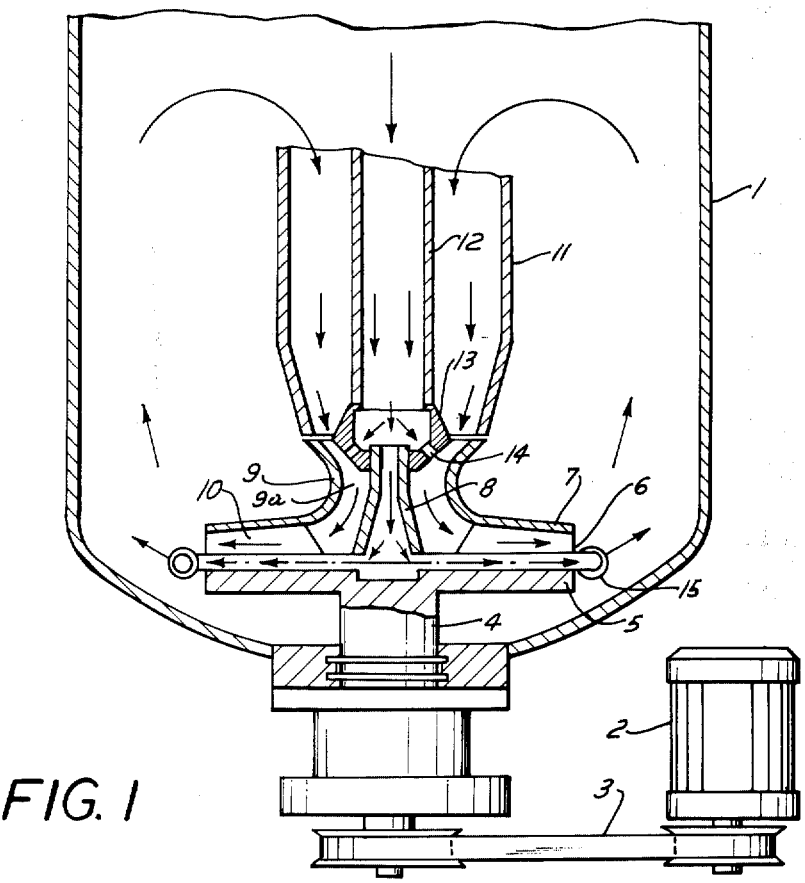
FIG. 1 is a vertical section through an arrangement according to the present invention.
Figure 2:
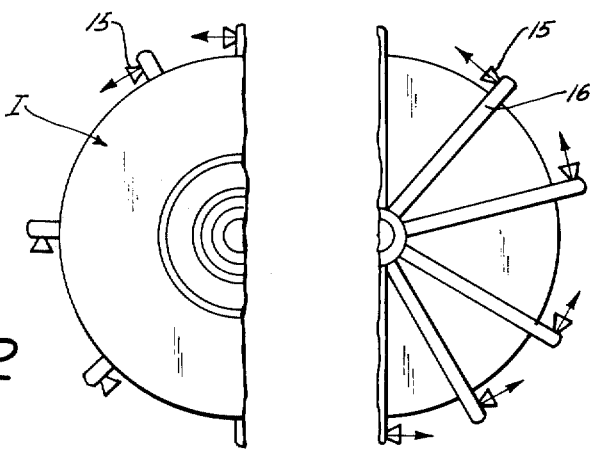
FIG. 2 is a top-plan view of the left-hand side of the impeller in the arrangement of FIG. 1.

DESCRIPTION OF THE PREFERRED EMBODIMENTS:

Referring firstly to FIGS. 1 and 2 it will be seen that reference numeral 1 identifies a vessel which is to contain a liquid to which gas must be admixed. In the illustrated embodiment the vessel 1 has a vertical orientation. Mounted in its interior is a rotary impeller I which has a hollow interior and is mounted on a shaft 4 that is driven via belts 3 by an electromotor 2. The impeller I is composed of two axially spaced disc members 5 and 7 and an intermediate disc member 6 which is fixedly mounted at a certain spacing above the disc member 5 and which carries at its center a hollow sleeve 8 which extends upwardly in form of a hub-like extension situated on the axis of rotation. In the region of the axis of rotation the disc member 7 is formed with a collar 9 which forms a passage having a venturi-like constrictions 9a through which liquid from the interior of the vessel 1 will be drawn when the impeller I rotates. Radially extending baffles 10 are mounted intermediate the disc members 6 and 7 and subdivide the spacing between them into passages which communicate with the constriction 9a and which have radially outer open ends located at the periphery of the impeller I. A guide baffle 11 for the liquid extends axially away from the collar 9 farther into the interior of the vessel 1 and terminates with its upper open end (not illustrated) in the manner conventional for mixers, fermenters and the like, with some spacing beneath the upper cover of the vessel 1. A lower end portion 13 of an air supply tube 12 partially surrounds the sleeve 8, and the tube 12 extends coaxially within the guide baffle 11. Gas outlet openings 14 are formed at the end portion 13 and communicate with the constriction 9a at or near the narrowest cross-sectional area thereof, so that the gas which is supplied in conventional manner (known per se and therefore not illustrated) through the air tube 12, can enter into the constriction 9a. When the impeller I rotates it draws liquid through the constriction 9a and expells it at the periphery of the impeller. This creates a suction at the throat of the constriction 9a, in the manner well known from all venturis, and this suction then draws the air through the outlet openings 14 from the tube 12, so that it can become admixed with the liquid flowing through the constriction 9a.

Thus far the construction is essentially known from the prior art. According to the present invention, however, I further provide a second system to admit the same type of gas, such as air or the like, as is admitted via the openings 14, or else to admit different kinds of gas. For this purpose the space defined between the disc members 5 and 6 receives a partial flow of the gas admitted via the tube 12, the flow being channeled into it by the sleeve 8. This space is formed at the periphery of the impeller I with outlet openings 15 that are formed in essentially funnel-shaped discharge members, the divergent ends of these discharge members facing opposite the direction of rotation of the impeller I. When the impeller I is rotated at high speed, a suction with eddy currents and cavitation will develop behind each of the portions 15, that is in the region of the wider outlet end thereof, drawing the gas from the space between the disc members 5 and 6 and providing for good admixture with the liquid.

Figure 3:
FIG. 3 is a view similar to FIG. 2, but illustrating the right-hand side of an impeller of a somewhat different embodiment.

The embodiment in FIG. 3 is largely the same as in FIG. 2 and can also be used in the arrangement of FIG. 1. In FIG. 3, however, the differences that the space between the disc member 5 and 6 accommodates radially mounted tubes or pipes 16 the radially outer ends of which are formed with the portions 15 having the outlet openings for the gas. In all other respects the embodiment of FIG. 3 is the same as that in FIG. 1 and 2.

Figure 4:
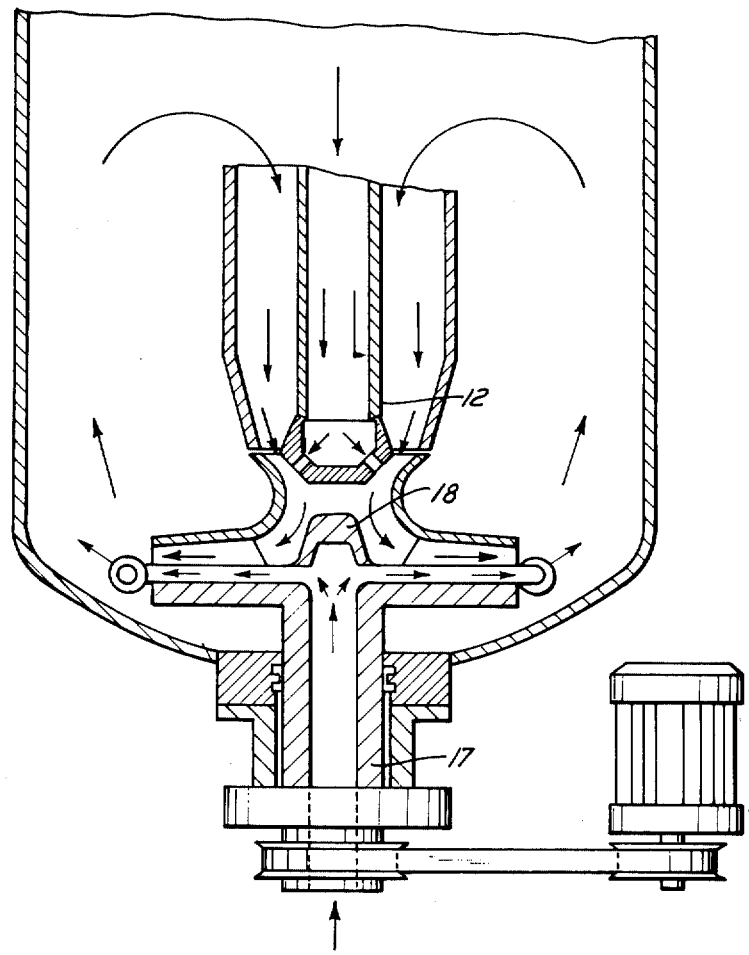
FIG. 4 is a view similar to FIG. 1 but illustrating a further embodiment of the invention.

FIG. 4, finally, shows another embodiment of the invention which is reminiscent of that in FIGS. 1 and 2 and differs from the same in that the supply of gas to the second system having the openings 15 is separate from the supply of gas to the openings 14. In this embodiment the drive shaft 17 for the impeller I is hollow and the gas to be discharged through the outlet openings 15 is admitted through the hollow interior of the shaft 17. In this embodiment the sleeve 8 of FIG. 1 is not required and is replaced by a hub 18 that is provided on the center disc member 6 and has only the purpose of improving the guidance of the liquid.

It will be appreciated that in order to be able to admit a gas through the hollow shaft 17 and appropriate seal must be provided such as an O-ring seal, a sliding ring seal, a stuffing box or the like, but this is well within the skill of those conversant with the art and need not be separately illustrated.

In this embodiment in particular it is very simple to provide appropriate throttles in the gas supply lines outside the vessel I, so that at any time the supply of gas being admitted can be readily controlled from the exterior. Moreover, this embodiment makes it possible to supply two different gases simultaneously and to keep them separated until they become admixed with the liquid in the vessel 1, which is important in certain applications, for example if those methane and air must be admitted to one and the same liquid and must therefore be kept apart until they actually become admixed with the liquid to prevent them from forming an explosive mixture.

It will be understood that each of the elements described above, or two or more together, may also find a useful application in other types of constructions differing from the types described above.

While the invention has been illustrated and described as embodied in the mixing of gas and liquid, it is not intended to be limited to the details shown, since various modifications and structural changes may be made without departing in any way from the spirit of the present invention.

Without further analysis, the foregoing will so fully reveal the gist of the present invention that others can be applying current knowledge readily adapt it for various applications without omitting features that, from the standpoint of prior art fairly constitute essential characteristics of the generic or specific aspects of this invention.

What is claimed as new and described to be protected by Letters Patent is set forth in the appended claims.

1. In an apparatus for mixing gas into liquids, particularly for aerating microorganisms in liquids, a combination comprising a vessel for a liquid; a hollow rotary impeller mounted for rotation in said vessel and having a venturi-shaped passage of hourglass configuration, comprised of an inlet in communication with the interior of said vessel and being located in the region of the axis of rotation of said impeller, an outlet located at the outer periphery of said impeller, and a throat located intermediate said inlet and said outlet and operative for drawing a stream of liquid through said passage in a first flow path; first gas outlet means including a plurality of first gas outlets located in said throat and communicating said throat with a source of gas so as to entrain the latter by the force of venturi suction prior to discharge of the resulting mixture through said outlet; means defining a separate second flow path for communicating a source of gas with said mixture at said outer periphery of said impeller; and second gas outlet means including a plurality of second gas outlets communicating with said separate means defining a second flow path, being located radially outwardly adjacent said outer periphery, and facing oppositely to the direction of rotation of said impeller for generating a suction force outwardly adjacent said outer periphery so as to draw the mixture in said first flow path outwardly from said hollow impeller into contact with the gas flowing in said second flow path, whereby a final mixture of finely-dispersed gas and liquid is obtained.--

2. A combination as defined in claim 1, wherein said second gas outlets have respective funnel-shaped divergent outlet portions which face opposite to the direction of rotation of said impeller.

3. A combination as defined in claim 1; further comprising a stationary gas supply tube having an opening adjacent said impeller; and a rotary sleeve mounted on said impeller for rotation therewith and extending into said opening said second gas outlets communicating with said sleeve to receive gas therefrom.

4. A combination as defined in claim 3, wherein a central axis of said sleeve and a central axis of said opening are both located on the axis of rotation of said impeller.

5. A combination as defined in claim 1; further comprising a first passage communicating with said first gas outlets to supply one gas thereto; and a seperate second passage communicating with said second gas outlets to supply another gas thereto.

6. A combination as defined in claim 5; further comprising a shaft mounting said impeller for rotation; and wherein said second passage is formed in said shaft.

7. A combination as defined in claim 1, said second gas outlets being rotatable with said impeller.

8. A method of injecting gases into a liquid accommodated in a vessel, particularly for aerating microorganisms in liquids, comprising the steps of rotating in said vessel a hollow rotary impeller having a venturi-shaped passage formed with an upper axial inlet, a lower outlet spaced from said inlet and being located at the outer periphery of said impeller, and at a throat located intermediate said inlet and lower outlet, drawing a stream of liquid by suction generated in said throat in a first flow path from said inlet through said passage to be expelled from said outlet; utilizing the suction generated in said throat for drawing gas into the stream of liquid flowing through said passage so as to form a resulting mixture; and expelling additional gas flowing in a separate second flow path into the mixture at the outer periphery of said impeller by generating a suction force outwardly adjacent said outer periphery, including the steps of locating a plurality of generally funnel-shaped gas outlets radially outwardly adjacent the outer periphery of said impeller, positioning said gas outlets so as to face in direction opposite to the direction of rotation of said impeller for drawing the mixture in said first flow path outwardly from said hollow impeller into contact with the additional gas flowing in said second flow path, and forming a final mixture of finely-dispersed gas and liquid.

9. A method as defined in claim 8, the step of expelling including the expelling of an additional gas having a character different from said gas drawn by suction into the liquid at its inlet into the impeller.

10. In an apparatus for mixing gas into liquids, particularly for aerating microorganisms in liquids, a combination comprising a vessel for a liquid; a hollow rotary impeller mounted for rotation in said vessel and having a venturi-shaped passage comprised of an upper inlet in communication with the interior of said vessel and being located in the region of the axis of rotation of said impeller, a lower outlet spaced from said inlet and being located at the outer periphery of said impeller, and a throat located intermediate said inlet and said outlet and operative for drawing a stream of liquid through said passage in a first flow path; first gas outlet means including a plurality of first gas outlets for communicating said throat with a source of gas so as to entrain the latter prior to discharge of the resulting mixture through said outlet; means defining a separate second flow path for communicating a source of gas with said mixture at said outer periphery of said impeller; and second gas outlet means including a plurality of second gas outlets communicating with said separate means defining a second flow path, and being located radially outwardly adjacent said outer periphery, said second gas outlets being generally funnel-shaped and facing oppositely to the direction of rotation of said impeller for generating a suction force outwardly adjacent said outer periphery so as to draw the mixture in said first flow path outwardly from said hollow impeller into contact with the gas flowing in said second flow path, whereby a final mixture of finely-dispersed gas and liquid is obtained.

* * * * *